United States Patent [19]
Asahi et al.

[11] Patent Number: 5,175,104
[45] Date of Patent: Dec. 29, 1992

[54] RECOMBINANT DNA AND A PROCESS FOR PRODUCING PHOSPHOTRANSACETYLASE

[75] Inventors: Matsuyama Asahi, Noda; Otake Hideko, Koshigaya; Nakano Eiichi, Iwatsuki, all of Japan

[73] Assignee: Kikkoman Corporation, Noda, Japan

[21] Appl. No.: 452,388

[22] Filed: Dec. 19, 1989

[30] Foreign Application Priority Data

Dec. 28, 1988 [JP] Japan .................. 63-329314

[51] Int. Cl.$^5$ .................. C12N 9/12; C12N 15/70; C12N 15/72
[52] U.S. Cl. .................. 435/194; 435/172.3; 435/252.33; 435/320.1
[58] Field of Search .................. 435/15, 188, 194; 935/29

[56] References Cited

PUBLICATIONS

Jacobs, et al., Nature 313:806-810, (1985).
Itaya, et al., (1967), Agr. Biol. Chem., 31:1256-1264
Van Holde, Physical Biochemistry, Prentice-Hall, 1971, p. 108.
Biochem. Biophys. Acta, 191, 550-558 (1969), Entitled: "Phosphotransacetylase of Escherichia Coli B, Purification and Properties" by Masao Shimizu, Tadao Suzuki, Kin--Ya-Kameda and Yasushi Abiko.

Primary Examiner—Richard A. Schwartz
Assistant Examiner—James Ketter
Attorney, Agent, or Firm—Banner, Birch, McKie & Beckett

[57] ABSTRACT

A novel recombinant DNA is characterized in that DNA containing a gene encoding phosphotransacetylase has been inserted into vector DNA. The recombinant DNA can be obtained by culturing in medium *E. coli* 1100 (pPT200) (FERM BP-2195) belonging to the genus Escherichia which contains a recombinant DNA obtained by inserting DNA containing a gene coding for phosphotransacetylase into vector DNA and is capable of producing phosphotransacetylase, and collecting phosphotransacetylase from the culture.

4 Claims, 1 Drawing Sheet

RECOMBINANT DNA AND A PROCESS FOR PRODUCING PHOSPHOTRANSACETYLASE

BACKGROUND OF THE INVENTION

1. Field of the Invention

The present invention relates to a novel recombinant DNA useful for production of phosphotransacetylase and to a process for producing phosphotransacetylase.

Phosphotransacetylase (EC 2.3.1.8, hereafter simply referred to as PTA) is an enzyme which catalyzes the formation of acetyl-CoA and phosphate from acetyl phosphate and coenzyme A (CoA). The reaction equation is shown below:

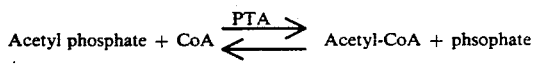

PTA can be used for the production and regeneration of acetyl-CoA and is also extremely useful as an enzyme for quantitative determination of acetyle-CoA, CoA an acetyle phosphate.

2. Description of the Prior Art

PTA has been hitherto produced by culturing, e. g., E. coli B, in medium and separating and purifying PTA from the cells [Biochim. Biophys. Acta, 191, 550–558 (1969)].

According to the aforesaid process of producing PTA, however, there were difficulties that yield of the enzyme is seriously poor, and the like.

SUMMARY OF THE INVENTION

Therefore, the present inventors have made various investigations to solve the difficulties described above. As a result, they have obtained a recombinant wherein DNA containing a PTA-encoding gene has been inserted into vector DNA and have found that PTA can be produced in a high yield by culturing a PTA-producing strain containing the recombinant belonging to the genus Escherichia in the medium. The present invention has thus been accomplished.

That is, the present invention deals with a novel recombinant DNA in which DNA containing a PTA-encoding gene has been inserted into vector DNA. The present invention also deals with a process for producing PTA which comprises culturing in medium PTA-producing strain belonging to the genus Escherichia which contains a recombinant DNA obtained by inserting a DNA containing PTA-encoding gene into vector DNA, and collecting PTA from the culture.

DESCRIPTION OF THE PREFERRED EMBODIMENTS

Figure 1:
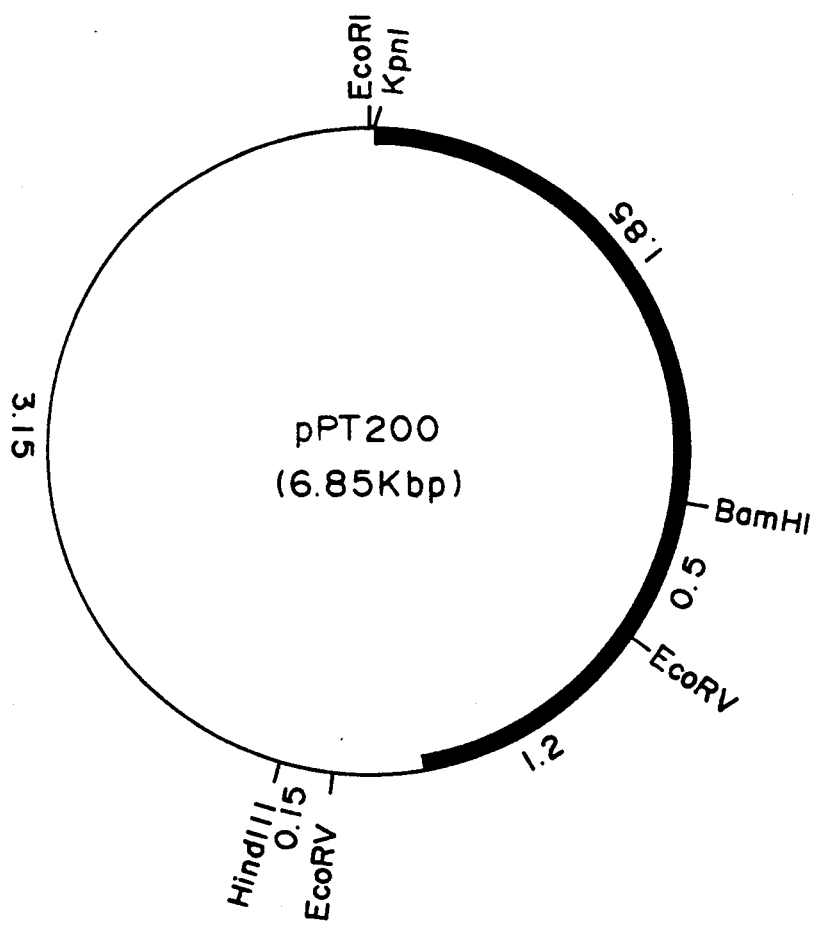
FIG. 1 shows a restriction enzyme cleavage map of the novel recombinant pPT200 plasmid DNA obtained in the present example.

Firstly, preparation of DNA containing PTA-encoding gene is described below.

A microorganism containing DNA containing PTA-encoding gene, for example, Escherichia coli 1100 (obtained from Max-Planck Institute, West Germany, Heiderberg) may be cultured by ordinary solid culture method but preferably by liquid culture method to give the culture.

As the medium for culturing the strain least one nitrogen source selected from yeast extract, peptone, meat extract, corn steep liquor, soybean or wheat bran, etc., which is supplemented with at least one of potassium primary phosphate, potassium secondary phosphate, magnesium sulfate, magnesium chloride, ferric chloride, ferric sulfate, manganese sulfate and the like; if necessary and desired, further suitably supplemented with glucide raw materials, vitamins, etc.

It is desired that the initial pH in the medium be adjusted to 7 to 9. It is also desired that the incubation be carried out at a temperature of 30 to 42° C., preferably at about 37° C., for 4 to 24 hours, preferably for 6 to 8 hours, by aerial spinner deep culture, shake culture, stationary culture, etc.

The culture solution is centrifuged at, e.g., more than 3000 r.p.m., preferably 8000 to 10000 r.p.m., for more than 5 minutes, preferably 10 to 15 minutes to give the cells of E. coli 1100 strain.

From the cells, chromosomal DNA can be obtained, for example, by the method of Saito and Miura [Biochim. Biophys. Acta, 72, 619 (1963)], the method of K. S. Kirby [Biochem. J., 64, 405 (1956)], etc.

Then, a staggered end forming restriction enzyme, e.g., Sau 3AI (manufactured by Toyobo Co., Ltd.) is acted on this chromosomal DNA at a temperature above 30° C., preferably 37° C., in an enzyme concentration of 1 to 10 units/ml for 20 minutes or longer, preferably for 0.5 to 2 hours to digest the chromosomal DNA, whereby a mixture of various chromosomal DNA fragments is obtained.

From the thus obtained DNA fragment mixture, the DNA fragment mixture is collected by, e.g., ordinary agarose gel electrophoresis and purified by a purifying means such as extraction with phenol, or the like. Further concentration by a concentrating means such as precipitation with ethanol, etc. gives the purified DNA fragment mixture (in which the DNA fragment containing PTA encoding gene is contained).

The vector DNA which can be used in the present invention may be any DNA and is exemplified by plasmid vector DNA, bacteriophage vector DNA and the like. Specific examples are preferably plasmid pBR322 DNA (manufactured by Bethesda Research Laboratories), plasmid pUC118 DNA (manufactured by Takara Shuzo Co., Ltd.), etc.

A staggered end-forming restriction enzyme, e.g., Bam HI (manufactured by Takara Shuzo Co., Ltd.) is acted on the vector DNA described above at a temperature above 30° C., preferably 37° C., in an enzyme concentration of 10 to 1000 units/ml for an hour or longer, preferably for 2 to 3 hours to digest the vector DNA, whereby cleaved vector DNA can be obtained.

Then, the E. coli 1100-derived DNA fragment mixture containing a PTA-encoding gene obtained as described above is mixed with the cleaved vector DNA and, for example, E. coli DNA ligase (manufactured by New England Bio Labs.), T4 DNA ligase (manufactured by Boehringer Mannheim), etc., preferably T4 DNA ligase, is acted on the mixture at a temperature of from 4 to 37° C., preferably 4 to 16° C., in an enzyme concentration of 1 to 100 units for an hour or longer, preferably for 6 to 24 hours to give the recombinant DNA.

Using the recombinant DNA, strains belonging to the genus Escherichia, for example, E. coli K-12, preferably E. coli HB101 (ATCC 33694), E. coli DH1 (ATCC 33849), E. coli -1776 (ATCC 31244), E. coli 1100 (obtained from Max-Planck Institut, West Germany, Heiderberg), *E. coli* JM101 (ATCC 33876), etc. are transformed or transduced to obtain the respective strains. The transformation can be effected by the method of D. M. Morrison [Methods in Enzymology, 68, 326-331 (1979)]. The transduction can be carried out by the method of B. Hohn [Methods in Enzymology, 68, 299-309 (1979)].

By screening the PTA-producing strain from the strains described above, the PTA-producing strain containing the recombinant DNA, wherein DNA containing a PTA-encoding gene has been inserted into vector DNA, and belonging to the genus *Escherichia* can be obtained.

To obtain the novel, purified recombinant DNA from the thus obtained strain, for example, the method of P. Guerry et. al. [J. Bacteriology, 116, 1064-1066 (1973)], the method of D. B. Cleweel [J. Bacteriology, 110, 667-676 (1972)], etc. are applicable.

To produce PTA using the thus obtained PTA-producing strain containing the recombinant DNA, wherein DNA containing a PTA-encoding gene has been inserted into vector DNA, and belonging to the genus Escherichia, the strain is cultured in the manner described above to obtain the culture.

After completion of the incubation, PTA can be collected from the culture in a conventional manner used for collecting enzyme.

For example, the cells are homogenized by ultrasonic wave or macerated in a conventional manner. Alternatively, lyzing enzyme such as lysozyme, etc. is used to extract the present enzyme. Further alternatively, the cells are shaken or allowed to stand in the presence of toluene or the like to effect self digestion and excrete the present enzyme out of the cells. The solution is filtered, centrifuged, etc. to remove the solid portion. If necessary and desired, nucleic acid is removed by streptomycin sulfate, protamine sulfate or manganese sulfate followed by fractionation with ammonium sulfate, alcohol, acetone, etc. After the precipitates are collected and dialyzed to water, the precipitates are dried in vacuum to give the crude enzyme.

To obtain the purified product of PTA, the crude product is purified by adsorption elution method using ion exchangers such as DEAE-cellulose (diethylaminoethyl cellulose, manufactured by Brown, USA), DEAE-Sephadex (diethylaminoethyl Sephadex, manufactured by Pharmacia Inc., Sweden), QAE-Sephadex (manufactured by Pharmacia Inc., Sweden), etc. Alternatively, the gel filtration method using Sephadex G-200 (manufactured by Pharmacia Inc., Sweden), Sepharose 6B (manufactured by Pharmacia Inc., Sweden), etc., the adsorption elution method using hydroxylapatite (manufactured by Biorad Inc., USA, BIOGEL HT), electrophoresis using polyacrylamide gel, etc. can be appropriately chosen and combined to obtain highly purified PTA product.

The physicochemical properties of PTA thus produced are quite identical with those of PTA described in Biochim. Biophys. Acta, 191, 550-558 (1969).

As is clear from the foregoing description, when the strain containing the novel recombinant DNA of the present invention which belongs to the genus Escherichia is cultured in medium, PTA can be efficiently obtained and therefore, the present invention is extremely useful from an industrial standpoint.

Hereafter the present invention is described in more detail by referring to the example.

EXAMPLE (1) Preparation of chromosomal DNA of *E. coli* 1100 strain

*E. coli* 1100 strain (obtained from Max-Planck Institut, West Germany, Heiderberg) was inoculated on 100 ml of T-Y medium [1% (W/V) Bactotrypton (manufactured by Difco Co., Ltd.), 0.5% (W/V) Bactoyeast extract (manufactured by Difco Co., Ltd.) and 0.5% (W/V) NaCl (pH 7.2)] and shake cultured at 37° C. for 8 hours to give the culture.

The culture was centrifuged at 10,000 r.p.m. for 15 minutes in a conventional manner to give 0.5 g of wet cells. From the wet cells, chromosomal DNA was obtained by the method of Saito and Miura [Biochim. Biophys. Acta, 72, 619 (1963)].

Then, 60 µg of this chromosomal DNA and 3 units of restriction enzyme Sau 3AI (manufactured by Toyobo Co., Ltd.) were mixed with 10 mM Tris-hydrochloride buffer (containing 50 mM NaCl, 10 mM $MgSO_4$ and 1 mM dithiothreitol, pH 7.4) followed by reacting at 37° C. for 30 minutes. After completion of the reaction, the reaction mixture was extracted with phenol in a conventional manner. In order to prevent renaturation of the DNA fragment digested with Sau 3AI, the DNA fragment was subjected to dephosphorylation by treating with bacterial alkaline phosphatase by the method described in Molecular Cloning, pages 133-134. Extraction with phenol and precipitation with ethanol in a conventional manner gave 50 µg of the chromosomal DNA fragment of *E. coli* 1100 strain digested with Sau 3AI.

(2) Preparation of recombinant plasmid pPT100 DNA

Plasmid pBR322 DNA (manufactured by Bethesda Research Laboratories), 10 µg, and 100 units of restriction enzyme Bam HI (manufactured by Takara Shuzo Co., Ltd.) were mixed with 50 mM Tris-hydrochloride buffer (containing 100 mM NaCl and 10 mM $MgSO_4$, pH 7.4) followed by reacting at 37° C. for 2 hours. The resulting digestion solution was extracted with phenol and precipitated with ethanol in a conventional manner to give plasmid pBR322 DNA digested with Bam HI.

Then 10 µg of plasmid pBR322 DNA digested with Bam HI, 10 µg of the chromosomal DNA fragment digested with Sau 3AI obtained in Item (1) and 5 units of T4 DNA ligase (manufactured by Boehringer Mannheim), were added to 66 mM Tris-hydrochloride buffer (pH 7.5) containing 6.6 mM $MgCl_2$, 10 mM dithiothreitol and 10 mM ATP. The mixture was reacted at 16° C. for 16 hours to ligate DNA. Thus, various recombinant plasmid DNAs were obtained.

Then, *E. coli* 1100 strain treated with calcium chloride by the method of D. M. Morrison [Methods in Enzymology, 68, 326-331 (1979)] was transformed by the thus ligated various recombinant plasmid DNAs to give 3000 transformants resistant to ampicillin and sensitive to tetracycline.

The following test was carried out to see if the PTA activity of the thus obtained transformants increased.

Each strain was inoculated on 1.5 ml of T-Y medium containing 50 µg/ml of ampicillin. Shake culture was conducted at a temperature of 30° C. for 24 hours to give the culture solution. The culture solution was centrifuged at 3,500 r.p.m. for 10 minutes to give wet cells. The cells were suspended in 10 mM phosphate buffer (pH 7.5) containing 10 mM $MgCl_2$ and 1 mM EDTA and 20 µl of toluene was added to the suspension. The mixture was shaken at a temperature of was added to 2.9 ml of 100 mM Tris-hydrochloride buffer (pH 8.0) containing 5 mM $MgCl_2$, 12, 0.5 mM AND, 0.5 mM CoA (coenzyme A), 5 mM L-malate, 12.5 μg/ml malate dehydrogenase, 25 μg/ml citrate synthase and 10 mM acetyl phosphate. By measuring change in absorption at 340 nm at a temperature of 25° C., the enzyme activity of PTA was determined. A transformant having a great change in absorption at 340 nm per hour shows increased enzyme activity. From the host E. coli 1100 strain, E. coli 1100 (pPT100) transformant was obtained.

(3) Isolation of recombinant plasmid pPT100 DNA

E. coli 1100 (pPT100) strain was precultured in medium containing 1% (W/V) of trypton, 0.5% (W/V) of yeast extract and 0.5% (W/V) of NaCl at a temperature of 37° C. for 24 hours. The thus obtained culture solution, 20 ml, was inoculated on 1 liter of the same medium. After shake culture at a temperature of 37° C. for 3 hours, 0.2 g of chloramphenicol was added to the culture solution. The mixture was cultured at the same temperature for further 20 hours to give the culture solution.

Then, the culture solution was centrifuged at 10,000 r.p.m. for 10 minutes in a conventional manner to give wet cells. After the wet cells were suspended in 20 ml of 50 mM Tris-hydrochloride buffer (pH 8.0) containing 25% (W/V) of sucrose, 10 mg of lysozyme, 8 ml of 0.25 M EDTA solution (pH 8.0) and 8 ml of 20% (W/V) of sodium dodecyl sulfate solution were added to the suspension. The mixture was kept at a temperature of 60° C. for 30 minutes to cause lysis. The lysate was thus obtained.

To the lysate was added 13 ml of 5 M NaCl solution and the mixture was treated at a temperature of 4° C. for 16 hours. The reaction mixture was centrifuged at 15,000 r.p.m. for 30 minutes in a conventional manner to give the extract. Treatment of the extract with ethanol and precipitation with phenol in a conventional manner gave the precipitates.

The precipitates were dried under reduced pressure in a conventional manner and dissolved in 6 ml of 10 mM Tris-hydrochloride buffer (pH 7.5) containing 1 mM EDTA. Furthermore, 6 g of cesium chloride and 0.2 ml of 10 mg/ml ethydium bromide were added to the solution. The mixture was subjected to equilibrium density gradient centrifugation at 39,000 r.p.m. for 42 hours in a conventional manner, using a ultracentrifuging machine to isolate the recombinant plasmid pPT100 DNA. Further after ethydium bromide was removed using n-butanol, dialysis was performed to 10 mM Tris-hydrochloride buffer (pH 7.5) containing 1 mM EDTA to give 1500 μg of the purified recombinant plasmid pPT100 DNA (the size was ca. 10.0 Kb).

(4) Preparation of novel recombinant plasmid pPT200 DNA

Plasmid pUC118 DNA (manufactured by Takara Shuzo Co., Ltd.), 0.2 μg, and 10 units of restriction enzyme Kpn I (manufactured by Takara Shuzo Co., Ltd.) were mixed with 10 mM Tris-hydrochloride buffer (containing 10 mM $MgCl_2$ and 1 mM dithiothreitol, pH 7.4) followed by reacting at a temperature of 37° C. for an hour. Furthermore, NaCl was added to become 50 mM NaCl and 10 units of restriction enzyme Hind III (manufactured by Takara Shuzo Co., Ltd.) followed by reacting at 37° C. for an hour. The resulting digestion solution was extracted with phenol and precipitated with ethanol in a conventional manner to give plasmid pUC118 DNA digested with Kpn I and Hind III.

Then, 1 μg of the recombinant plasmid pPT100 DNA obtained in Item (3) and 10 units of Kpn I were mixed with 10 mM Tris-hydrochloride buffer (containing 10 mM $MgCl_2$ and 1 mM dithiothreitol, pH 7.4). After the mixture was reacted at 37° C. for an hour, NaCl was added thereto to become the final concentration of 50 mM. To the mixture were added 10 units of restriction enzyme Hind III. The mixture was reacted at a temperature of 37° C. for an hour to give the digestion solution.

The digestion solution was subjected to 0.7 % (W/V) agarose gel electrophoresis and then eluted by the method of R. C. A. Yang et. al. [Methods in Enzymology, 68, 176–182 (1979)] to give the eluate. The eluate was extracted with phenol and precipitated with ethanol in a conventional manner to give 0.3 μg of the DNA fragment.

0.3 μg of the plasmid pUC118 DNA digested with Kpn I and Hind III and 0.3 μg of the 3.3 Kbp DNA fragment digested with Kpn I/Hind III derived from pPT100 plasmid DNA were dissolved in 7 μl of water. To the solution were added 13 μl of a mixture [77 mM Tris-hydrochloride buffer (pH 7.4)/15 mM $MgCl_2$/15 nM dithiothreitol/0.15 mM ATP] and 1 unit of T4 DNA ligase. Ligation was effected at a temperature of 8° C. for 18 hours Using the reaction solution, E. coli 1100 strain (ATCC 33876) was transformed by the transformation method described in Journal of Bacteriology, 119, 1072–1074 (1974)]. Chemical resistance (ampicillin resistance) and β-galactosidase activity were examined to obtain a transformant. Plasmid DNA was isolated from this transformant and designated pPT200. The thus obtained E. coli 1100 (pPT200) has been deposited in the Fermentation Research Institute of the Agency of Industrial Science & Technology, 1-3 Higaski / Chrome, Tsukula-shi, Ilaroki-ken, 305, Japan as the Accession Number of FERM BP-2195 under the Budapest Treaty, on Dec. 16, 1988.

(5) Culture of E. coli 1100 (pPT200) and preparation of crude enzyme solution

E. coli 1100 (pPT200) (FERM BP-2195) obtained in Item (4) was shake-cultured at a temperature of 37° C. for 18 hours in 3 ml of LB-amp medium [1% (W/V) Bactotrypton, 0.5% (W/V) yeast extract, 0.5% (W/V) NaCl and 50 μg/ml of ampicillin] to give the culture solution. The thus obtained culture solution, 0.5 ml, was inoculated on 10 ml of LB-amp medium described above containing 10 mM of isopropyl-B-D-thiogalactoside. After shake culture at a temperature of 37° C. for 6 hours, centrifugation was performed at 3,500 r.p.m. for 10 minutes to give wet cells. The wet cells were suspended in 1 ml of 10 mM phosphate buffer (pH 7.5) containing 10 mM $MgCl_2$ and 1 mM EDTA. The suspension was homogenized by ultrasonic wave in a conventional manner to give the crude enzyme solution. The PTA activity in the thus obtained crude enzyme solution was determined by the following method.

The aforesaid crude enzyme solution, 100 μl, was added to 2.9 ml of 100 mM Tris-hydrochloride buffer (pH 8.0) containing 5 mM $MgCl_2$, 0.5 mM NAD, 0.5 mM CoA, mM L-malate, 12.5 μg/ml of malate dehydrogenase, 25 g/ml of citrate synthase and 10 mM acetyl phosphate. The amount of NADH formed was calculated from change in absorption at 340 nm at a temperature of 25° C. The results are shown in the table below.

Also for purpose of comparison, the PTA activity was determined likewise with *E. coli* 1100 strain [*E. coli* 1100 (pUC118)] containing plasmid pUC118 DNA. The results are also shown in the following table.

TABLE

| | Strain | Item<br>Amount of NADH Formed<br>($\mu$mol/mg protein/min) |
|---|---|---|
| Invention: | *E. coli* 1100<br>(pPT200) | 203.6 |
| Comparison: | *E. coli* 1100<br>(pUC118) | 1.7 |

As is evident from the table above, the crude enzyme solution obtained by the present invention obviously shows markedly increased amount of NADH formed as compared to the crude enzyme solution for comparison, indicating that PTA is expressed in the crude enzyme solution of the present invention.

(6) Preparation of recombinant plasmid pPT200 DNA containing PTA gene

*E. coli* 1100 (pPT200) strain (FERM BP-2195) obtained in Item (5) described above was precultured in liter of medium containing 1% (W/V) of trypton, 0.5% (W/V) of yeast extract and 0.5% (W/V) of NaCl at a temperature of 37° C. for 24 hours. The thus obtained culture solution, 20 ml, was inoculated on 1 liter of the same medium. After shake culture at a temperature of 37° C. for 3 hours, 0.2 g of chloramphenicol was added to the culture solution. The mixture was cultured at the same temperature for further 20 hours to give the culture solution.

Then, the culture solution was centrifuged at 6,000 r.p.m. for 10 minutes in a conventional manner to give 2 g of wet cells. After the wet cells were suspended in 20 ml of 350 mM Tris-hydrochloride buffer (pH 8.0) containing 25% (W/V) of sucrose, 10 mg of lysozyme (manufactured by Sigma Co., Ltd.), 8 ml of 0.25 mM EDTA solution (pH 8.0) and 8 ml of 20% (W/V) sodium dodecyl sulfate solution were added to the suspension. The mixture was kept at a temperature of 60° C. for 30 minutes to cause lysis. The lysate was thus obtained. To the lysate was added 13 ml of 5 M NaCl aqueous solution and the mixture was treated at a temperature of 4° C. for 16 hours. The reaction mixture was centrifuged at 15,000 r.p.m. for 30 minutes in a conventional manner to give the extract. Treatment of the extract with ethanol and precipitation with phenol in a conventional manner gave the precipitates.

The precipitates were then dried under reduced pressure in a conventional manner and dissolved in 6 ml of 10 mM Tris-hydrochloride buffer (pH 7.5) containing 1 mM EDTA. Furthermore, 6 g of cesium chloride and 0.2 ml of ethydium bromide (19 mg/ml) were added to the solution. The mixture was subjected to equilibrium density gradient centrifugation at 39,000 r.p.m. for 42 hours in a conventional manner, using a ultracentrifuging machine to isolate the recombinant plasmid pPT200 DNA. Further after ethydium bromide was removed using n-butanol, dialysis was performed to 10 mM Tris-hydrochloride buffer (pH 7.5) containing 1 mM EDTA to give 600 $\mu$g of the purified recombinant plasmid pPT200 DNA.

The recombinant plasmid pPT200 DNA was subjected to single digestion and double digestion using restriction enzymes Eco RI, Kpn I, Bam HI, Eco RV and Hind III (all manufactured by Takara Shuzo Co., Ltd.). The resulting DNA fragments were analyzed with mobility pattern by agarose electrophoresis. By comparing the obtained mobility pattern with the standard mobility pattern of the DNA fragments obtained by digesting bacteriophage λ DNA (manufactured by Takara Shuzo Co., Ltd.) with Hind III, the restriction enzyme cleavage map was obtained as shown in FIG. 1.

What is claimed is:

1. A recombinant DNA in which DNA containing a gene encoding phosphotransacetylase has been inserted into vector DNA.

2. A recombinant DNA as claimed in claim 1, wherein said DNA containing a gene encoding phosphotransacetylase is DNA derived from *Escherichia coli* 1100 strain.

3. A recombinant DNA as claimed in claim 1, wherein said vector DNA is plasmid pBR322 or pUC118 DNA.

4. A process for producing phosphotransacetylase which comprises culturing in medium a phosphotransacetylase-producing strain *Escherichia coli* 1100 (pPT200) (FERM BP-2195) belonging to the genus *Escherichia* which contains a recombinant DNA obtained by inserting DNA containing phosphotransacetylase-encoding gene into vector DNA, and collecting phosphotransacetylase from the culture.

* * * * *